(12) United States Patent
Fernandes et al.

(10) Patent No.: US 7,387,645 B2
(45) Date of Patent: Jun. 17, 2008

(54) CELLULAR THERAPY TO HEAL VASCULAR TISSUE

(75) Inventors: Brian Fernandes, Roseville, MN (US); Jack Chu, Santa Rosa, CA (US); Prema Ganesan, San Francisco, CA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 154 days.

(21) Appl. No.: 10/423,193

(22) Filed: Apr. 25, 2003

(65) Prior Publication Data

US 2004/0215334 A1 Oct. 28, 2004

(51) Int. Cl.
*A61F 2/02* (2006.01)
*A01N 63/00* (2006.01)
*A61K 48/00* (2006.01)

(52) U.S. Cl. .................................. 623/23.75; 424/93.2
(58) Field of Classification Search .............. 623/23.75; 128/898; 424/93.2
See application file for complete search history.

(56) References Cited

U.S. PATENT DOCUMENTS

| | | | |
|---|---|---|---|
| 5,486,359 A | 1/1996 | Caplan et al. | |
| 5,538,504 A | 7/1996 | Linden et al. | |
| 5,667,778 A * | 9/1997 | Atala | 424/93.7 |
| 5,670,161 A | 9/1997 | Healy et al. | |
| 5,713,917 A | 2/1998 | Leonhardt et al. | |
| 5,843,781 A * | 12/1998 | Ballermann et al. | 435/400 |
| 6,096,347 A | 8/2000 | Geddes et al. | |
| 6,151,525 A | 11/2000 | Soykan et al. | |
| 6,152,943 A * | 11/2000 | Sawhney | 606/193 |
| 6,159,239 A | 12/2000 | Greenhalgh | |
| 6,190,353 B1 | 2/2001 | Makower et al. | |
| 6,287,315 B1 | 9/2001 | Wijeratne et al. | |
| 6,302,870 B1 | 10/2001 | Jacobsen et al. | |
| 6,344,035 B1 | 2/2002 | Chudzik et al. | |
| 6,348,050 B1 | 2/2002 | Hartlaub | |
| 6,364,903 B2 | 4/2002 | Tseng et al. | |
| 6,368,346 B1 | 4/2002 | Jadhav | |
| 6,371,970 B1 | 4/2002 | Khosravi et al. | |
| 6,376,742 B1 | 4/2002 | Zdrahala et al. | |
| 6,387,121 B1 | 5/2002 | Alt | |
| 6,429,013 B1 | 8/2002 | Halvorsen et al. | |
| 6,451,373 B1 | 9/2002 | Hossainy et al. | |
| 6,497,875 B1 | 12/2002 | Sorrell et al. | |

(Continued)

FOREIGN PATENT DOCUMENTS

WO WO 00/34442 * 6/2000

(Continued)

OTHER PUBLICATIONS

Chaikof, Elliot L. et al. "Biomaterials and Scaffolds in Reparative Medicine," *Annals New York Academy of Sciences* 2002, 961:96-105.

(Continued)

*Primary Examiner*—Thomas J Sweet
(74) *Attorney, Agent, or Firm*—Michelle Glasky; Sally Brashears (57) ABSTRACT

The present invention encompasses methods and apparatus for minimizing the risks inherent in endovascular grafting for blood vessel therapy and repair. The invention involves delivering adult stem cells, embryonic stem cells, progenitor cells, fibroblasts, or smooth muscle cells to the diseased blood vessel.

19 Claims, 4 Drawing Sheets

U.S. PATENT DOCUMENTS

| | | | |
|---|---|---|---|
| 6,506,410 | B1 | 1/2003 | Park et al. |
| 6,514,515 | B1 | 2/2003 | Williams |
| 6,531,154 | B1 | 3/2003 | Mathiowitz et al. |
| 6,767,358 | B2 | 7/2004 | Leonhardt et al. |
| 2002/0065546 | A1 | 5/2002 | Machan et al. |
| 2003/0118567 | A1* | 6/2003 | Stewart ................ 424/93.21 |
| 2004/0234972 | A1* | 11/2004 | Owens et al. .............. 435/6 |

FOREIGN PATENT DOCUMENTS

| | | |
|---|---|---|
| WO | WO 02/12539 A2 * | 2/2002 |
| WO | WO-02/15824 A2 | 2/2002 |

OTHER PUBLICATIONS

Griffith, Linda G. "Emerging Design Principles in Biomaterials and Scaffolds or Tissue Engineering," *Annals New York Academy of Sciences* 2002, 961: 83-95.

Ochoa, Erin R. et al. "An Overview of the Pathology and Approaches to Tissue Engineering." *Annals New York Academy of Sciences* 2002, 979: 10-26.

Goodman, Louis Sanford and Albert Gilman.*The Pharmacological Basis of Therapeutics*. New York: McGraw-Hill, 2001.

Gulbins, H. et al. "Cell Transplantation—a potential therapy for cardiac repair in the future?" *Heart Surg Forum* 2002, 5(4):E28-34. *National Center for Biotechnology Information*. Mar. 5, 2003 <http://www.ncbi.nlm.nih.gov/entrez/query.fcgi?cmd=Retrieve&db=PubMed&list_uids=12538127&dopt=Abstract>.

Chiu, Ray C.-J. et al. "Cellular Cardiomyoplasty: Myocardial Regeneration With Satellite Cell Implantation." *Ann Thorac Surg* 1995, 60:12-18.

Oishi, Kazuhiko et al. "Contractile responses of smooth muscle cells differentiated from rat neural stem cells." *Journal of Physiology* 2002, 540.1: 139-152.

Naito, H et al. "Embryonic stem cell-derived cardiomyocyte transplantation into the infarcted myocardium." *Heart Surg Forum* 2002, 6(1): *National Center for Biotechnology Information*. Mar. 5, 2003 <http://www.ncbi.nlm.nih.gov/entrez/query.fcgi?cmd=Retrieve&db=PubMed&List_uids=12611685&dopt=Abstract>.

Liechty, Kenneth W. et al. "Human mesenchymal stem cells engraft and demonstrate site-specific differentiation after in utero transplantation in sheep." *Nature Medicine* Nov. 2000. 6.11:1282-1286.

Zhao, Yong et al. "A human peripheral blood monocyte-derived subset acts as pluripotent stem cells." *Proceedings of the National Academy of Sciences of the United States of America* Mar. 4, 2003, 100.5: 2426-2431.

Noishiki, Yasuharu et al. "Introduction of Tissue Engineering Concepts into the Field of Endovascular Grafts: An Attempt to Solve Endoleakage Problems of Endovascular Grafts Implanted in Aortic Aneurysms." *Artificial Organs* 2001, 25(3):228-235.

Toma, Jean G. et al. "Isolation of multipotent adult stem cells from the dermis of mammalian skin." *Nature Cell Biology* Sep. 2001, 3:778-784.

Min, JY et al. "Long-term improvement of cardiac function in rats after infarction by transplantation of embryonic stem cells." *J Thorac Cardiovasc Surg* Feb. 2003, 125(2): 361-369. *National Center for Biotechnology Information*. Mar 5, 2003<http://www.ncbi.nlm.nih.gov/entrez/query.fcgi?cmd=Retrieve&db=PubMed&list_uids=12579106&dopt=Abstract>.

Oshima, H. et al. "Long-term survival of novel muscle-derived stem cells after transplantation into myocardium." *Heart Surg Forum* 2002, 6(1): 7. *National Center for Biotechnology Information*. Mar. 5, 2003<http://www.ncbi.nlm.nih.gov/entrez/query.fcgi?cmd=Retrieve&db=PubMed&list_uids=12611715&dopt=Abstract>.

Zuk, Ph.D., Patricia A. et al. "Multilineage Cells from Human Adipose Tissue: Implications for Cell-Based Therapies." *Tissue Engineering* 2001, 7.2: 211-228.

Jiang, Yuehua et al. "Pluripotency of mesenchymal stem cells derived from adult marrow." *Nature* Jul. 2002, 418: 41-49.

Frankish, Helen. "Researchers turn human stem cells into heart tissue." *The Lancet* Aug. 2001, 358: 475.

Simper, MD, David et al. "Smooth Muscle Progenitor Cells in Human Blood." *Circulation* 2002, 106: 1199-1204.

US 6,348,062, 02/2002, Hopkins et al. (withdrawn)

* cited by examiner

CELLULAR THERAPY TO HEAL VASCULAR TISSUE

BACKGROUND OF THE INVENTION

Aortic aneurysms and the degeneration of the vasculature in general represent a significant medical problem for the general population. Aneurysms within the aorta presently affect between two and seven percent of the general population and the rate of incidence appears to be increasing. This form of vascular disease is characterized by degeneration in the arterial wall in which the wall weakens and balloons outward. Until the affected artery is grafted through open repair or treated with a stent graft endovascularly, a patient with an aortic aneurysm must live with the threat of aortic aneurysm rupture and death.

One known clinical approach for patients with an aortic aneurysm is a surgical repair procedure. This is an extensive operation involving dissection of the aorta and reinforcement of the aneurysm wall with a prosthetic graft.

Alternatively, there is a significantly less invasive clinical approach to aneurysm repair known as endovascular grafting. Endovascular grafting involves the placement of a prosthetic arterial stent graft within the lumen of the artery. To prevent rupture of the aneurysm, a stent graft of tubular construction is introduced into the blood vessel, and is secured in a location such that the stent graft spans the length of the aneurysmal sac. The outer surface of the stent graft at its ends is sealed to the interior wall of the blood vessel at a location where the blood vessel wall has not suffered a loss of strength or resiliency, such that blood flowing through the vessel is diverted through the hollow interior of the stent graft away from the blood vessel wall at the aneurysmal sac location. In this way, the risk of rupture of the blood vessel wall at the aneurysmal location is significantly reduced and blood can continue to flow through to the downstream blood vessels without interruption. However, despite the advantages of endovascular grafting over other surgical procedures, there is, nonetheless, continued progression of the aneurysm disease.

A salient feature of aneurysm formation is the gradual degradation of extracellular components, such as collagen and elastin, as well as the loss of resident cells, namely smooth muscle cells and fibroblasts. The cells in a healthy vessel perform many and varied functions, including providing reinforcement to the vessel wall and, importantly, replenishing the extracellular components. The diminished cellular presence observed in diseased arteries directly and adversely impacts the vessel wall ultrastructure.

The field of cell replacement research and tissue engineering currently is one of the major focuses of medical technology. An exciting area of tissue engineering is the emerging technology of "self-cell" therapy, where cells of a given tissue type are removed from a patient, isolated, perhaps mitotically expanded and/or genetically engineered, and ultimately reintroduced into the donor/patient with or without synthetic materials or other carrier matrices. One goal of self-cell therapy is to help guide and direct the rapid and specific repair or regeneration of tissues. Such self-cell therapy is already a part of clinical practice; for example, using autologous bone marrow transplants for various hematologic conditions. The rapid advancement of this technology is reflected in recent publications that disclose progress toward bone and cartilage self-cell therapy. Moreover, similar advances are being made with other tissues such as cardiac muscle, liver, pancreas, tendon and ligament. One of the greatest advantages of self-cell therapy over current technologies is that the autologous nature of the tissue/cells greatly reduces, if not eliminates, immunological rejection and the costs associated therewith.

Thus there is a desire in the art to slow, reverse, or potentially cure the aneurysm disease state by using minimally invasive procedures while reducing or eliminating immunological rejection. The present invention satisfies this need in the art.

SUMMARY OF THE INVENTION

The present technology addresses the problem of degeneration of vascular tissue, particularly at an aneurysmal site. Embodiments according to the present invention provide methods for supporting and treating the vascular tissue with fully differentiated primary cells, such as fibroblasts or smooth muscle cells, as well as stem cells derived from adult sources. Such cells function to replace, regenerate, reinforce and strengthen the disease site through the secretion of extracellular matrix components in the tissue wall.

Thus, in one embodiment, there is provided a method of treating a blood vessel in an individual comprising: harvesting tissue from the individual; isolating cells of one or more cell type from the harvested tissue; and delivering the isolated cells to the blood vessel by a delivery means. In one aspect, single cell populations or combination cell populations (which include more than one cell type) are used. In another aspect of the embodiment of this invention, the isolated cells are expanded or differentiated in vitro before delivery. In another aspect of the embodiment of this invention, the cells are genetically engineered in vitro before delivery. In another aspect of this embodiment of the invention, the cells are delivered in conjunction with a carrier and/or cellular scaffold and are left to expand, and, if necessary, differentiate in vivo. In another aspect of the embodiment, the cells are delivered together with agents, such as growth factors, to promote or enhance cell proliferation and/or secretion in vivo.

BRIEF DESCRIPTION OF THE DRAWINGS

A more particular description of the invention, briefly summarized above, may be had by reference to the embodiments of the invention described in the present specification and illustrated in the appended drawings. It is to be noted, however, that the specification and appended drawings illustrate only certain embodiments of this invention and are, therefore, not to be considered to be limiting of its scope. The invention may admit to equally effective embodiments as defined by the claims.

DETAILED DESCRIPTION

Reference will now be made in detail to exemplary embodiments of the invention. While the invention will be described in conjunction with these embodiments, it is to be understood that the described embodiments are not intended to limit the invention solely and specifically to only these embodiments. On the contrary, the invention is intended to cover alternatives, modifications, and equivalents that may be included within the spirit and scope of the invention as defined by the attached claims.

The present technology encompasses methods for treating the aneurysm wall of blood vessels in an individual. Aspects of the invention include a method for delivering adult stem cells, including progenitor cells, derived from, for example, adipose tissue, bone marrow, or peripheral blood of the individual, to a blood vessel in need of therapy. Also included are methods for the delivery of differentiated primary cells, such as vascular smooth muscle cells or fibroblasts, derived from, for example, arterial or venous blood vessel segments and dermal tissue (skin), respectively. The stem cells, fibroblasts, or smooth muscle cells to be delivered may come directly from the adipose tissue, bone marrow, or other tissue samples, or the cells may be cultured, expanded or manipulated before delivery. One cell type or a combination of cell types may be delivered. In addition, the cells may be delivered along with a natural or synthetic cellular scaffolding material and/or carrier solution, and with or without bioactive agents.

Figure 1:
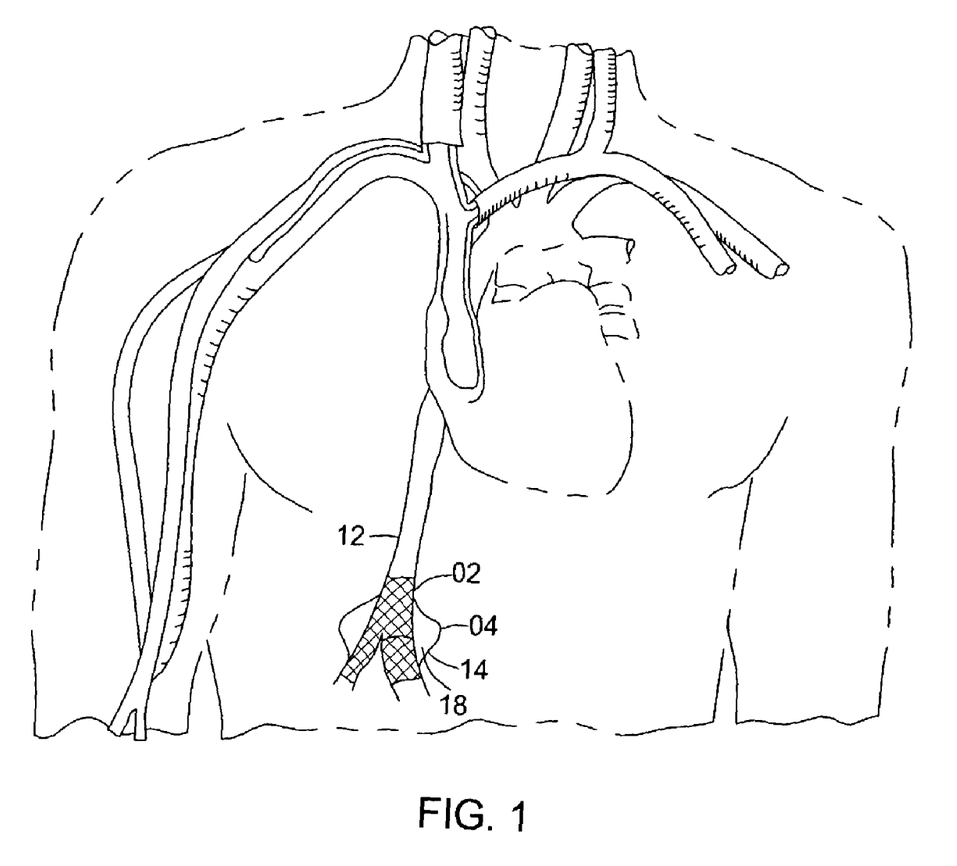
FIG. 1 is a schematic view of a human aortal aneurysm.

Referring initially to FIG. 1, there is shown generally an aneurysmal blood vessel; in particular, there is an aneurysm of the aorta 12, such that the aorta or blood vessel wall 04 is enlarged at an aneurysmal site 14 and the diameter of the aorta 12 at the aneurysmal site 14 is larger than the diameter of a healthy aorta 12. The aneurysmal site 14 forms an aneurysmal bulge or sac 18. If left untreated, the aneurysmal sac 18 may continue to deteriorate, weaken, increase in size, and eventually tear or burst.

As stated previously, vascular surgery and endovascular grafts have proven successful in patients with aortic aneurysms; however, neither procedure inhibits the progression of the disease state. Before the aneurysm reaches a size to necessitate such procedures, the present invention treats blood vessels directly—particularly at the site of an aneurysm, possibly preventing the need for subsequent surgical repair. Alternatively, the present invention can be used in addition to surgery or placement of a stent graft to bolster and provide enhanced healing at the aneurysmal site. Such methods involve tissue engineering using self-derived cells, or, alternatively, immuno-neutral non-self-derived stem cells (for example, mesenchymal stem cells) may be used.

Progression of the disease state is characterized by continued degeneration of the aortic wall due to thinning of the medial connective tissue architecture of the aorta, and a concomitant loss of collagen in the adventitia associated with dilatation of the vessel. There is evidence that connective tissue-degrading enzymatic activity is triggered by inflammation in the medial and adventitial layers of the aorta. Accordingly, one aspect of one embodiment of the present invention involves limiting the spread of inflammation by implantation of stem cells, progenitor cells, or smooth muscle cells into the blood vessel wall such that the newly created vascular smooth muscle exerts a paracrine, protective effect against artery wall destruction by inflammation. The smooth muscle cells and fibroblasts in this normal in vivo setting thus are likely to synthesize aortic wall collagen (type I & III) and elastin. Thus, among other advantages, the invention provides the blood vessel with therapy that protects and regenerates extracellular matrix components in the medial and adventitial layers of blood vessels, preventing continued dilatation and/or further degeneration of the aortic tissue.

Figure 2:
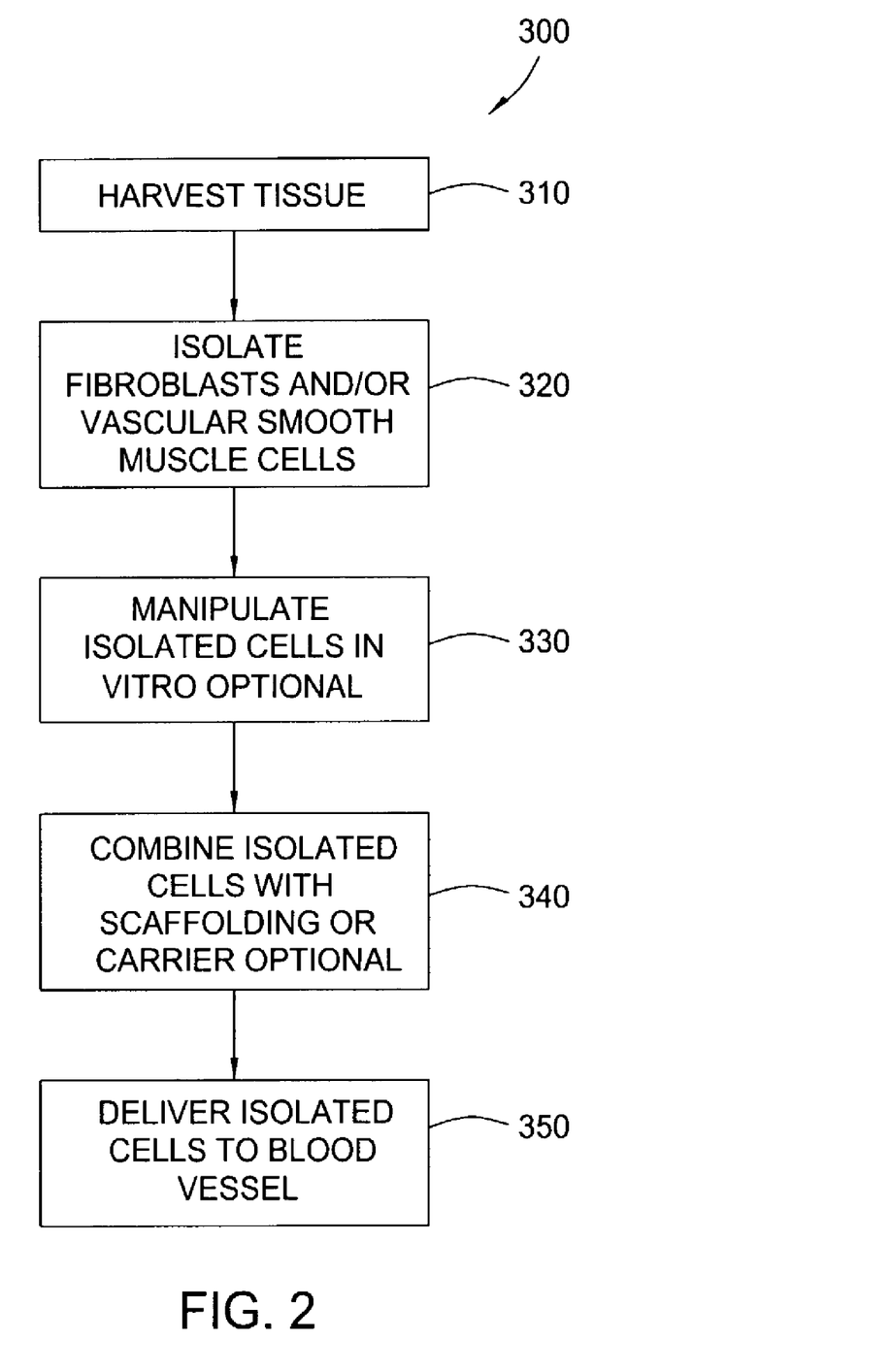
FIG. 2 is a flow chart of one embodiment of the methods of the present invention.

FIG. 2 is a flow chart of one embodiment of methods according to the present invention. In FIG. 2, method 300 is comprised of three main steps and two optional steps. In step 310, tissue is harvested from, for example, adipose tissue, bone marrow, blood or other tissues where stem cells and/or smooth muscle cells may be found. For example, adipose tissue is readily accessible and abundant in most individuals and can be harvested by liposuction. Various liposuction techniques exist, including ultrasonic-assisted liposuction ("UAL"), laser-assisted liposuction, and traditional suction-assisted liposuction ("SAL"), where fat is removed with the assistance of a vacuum created by either a mechanical source or a syringe. Each of the foregoing liposuction techniques may be used in conjunction with tumescent solution. Liposuction procedures that use a tumescent solution generally involve pre-operative infiltration of subcutaneous adipose tissue with large volumes of dilute anesthetic solutions. The evolution of the tumescent technique has revolutionized liposuction by making it available on an outpatient basis. Specifically, it makes the use of general anesthesia optional in most cases thereby avoiding the associated risks and costs. (See, e.g., Rohrich, et al., *Plastic and Reconstructive Surgery*, 99:514-19 (1997).)

Another advantage of using adipose tissue as a source of stem cells is that, due to the abundance of stem cells in adipose tissue, stem cell harvest, isolation, genetic manipulation and/or growth-factor based differentiation may be accomplished perioperatively. Thus, depending on the number of cells required for implantation, it may not be necessary for the patient to submit to the liposuction procedure on one day and the stem cell implantation on a subsequent day. The procedures can be performed sequentially within minutes or tens of minutes of one another. (See, e.g., Noishiki, et al., *Artificial Organs*, 25(3):228-35 (2001); and Zuk, et al., *Tissue Engineering*, 7(2):211-28).

Alternatively, bone marrow may be harvested for vascular smooth muscle cell or fibroblast isolation. As a whole, bone marrow is a complex tissue comprised of two distinct populations of stem cells, namely hematopoietic stem cells and mesenchymal stem cells. Hematopoietic stem cells give rise to components of the blood and immune systems while mesenchymal stem cells give rise to varied cells, including osteoblasts, chondrocytes, adipocytes, fibroblasts, smooth muscle cells, and myoblasts. Cells, such as fibroblasts, reticulocytes, adipocytes, and endothelial cells, form a connective tissue network called "stroma". Cells from the stroma regulate morphologically the differentiation of hematopoietic cells through direct interaction via cell surface proteins and the secretion of growth factors. Stroma cells also are involved in the foundation and support of the bone structure. Studies using animal models show that bone marrow contains "pre-stromal" cells which have the capacity to differentiate into cartilage, bone, and other connective tissue cells, and, in an inverse relationship with age, they are capable of differentiating into an assortment of connective tissues depending upon the influence of a number of bioactive factors. While mesenchymal stem cells are extremely rare in bone marrow, they also can be found in other tissues, such as peripheral blood, umbilical cord blood and adipose tissue.

In certain embodiments according to the present invention, an autologous bone marrow transplant is contemplated. In an autologous transplant, the individual to receive therapy donates his or her own stem cells for later reinfusion. The procedure for harvesting bone marrow from the individual is performed while the individual is under anesthesia. A needle is inserted into the cavity of the rear hip bone, the iliac crest, where a large quantity of bone marrow is located. The bone marrow is a thick, red liquid and is extracted by a syringe. Several skin punctures on each hip and multiple bone punctures may be required to harvest enough stem cells for use in the present invention.

In yet another embodiment, smooth muscle cells may be derived from peripheral blood. Human blood has circulating adult progenitor cells that are capable of differentiating into smooth-muscle-like cells in response to platelet derived growth factor (PDGF-BB) treatment. (See, e.g., Simper, et al., *Circulation*, 106:1199-1204 (2002)). Thus, in one embodiment of the present invention, a blood draw is contemplated. Since progenitor cell populations are present in very low percentages, the cells are expanded in culture following growth factor-induced differentiation and selection. Alternatively, the patients may be systemically treated with agents, such as granulocyte-colony stimulating factor (G-CSF), granulocyte monocyte colony-stimulating factor (GM-CSF), or the like, which are known to increase hematopoietic progenitors in humans by activating and promoting mobilization of these progenitors from bone marrow into the circulation by several fold.

In a next step, step 320 of FIG. 2, cells are isolated from the harvested tissue. In general, methods of isolation of cells includes not only harvesting a tissue specimen, but also processing the specimen so that the cells contained therein are substantially dissociated into single cells rather than grouped as cell clusters. Dissociating the cells into single cell components can be accomplished by any method known in the art; e.g., by mechanical (filtering) or enzymatic means. Further, in the case of stem cells, the isolating step includes combining the stem cell-containing specimen with a cell culture medium comprising factors that (i) stimulate fibroblast or vascular smooth muscle stem cell growth without differentiation, and (ii) allow expansion of substantially only the stem cells. Next, the specimen-medium mixture is cultured for a few to many cell passages.

Protocols for the identification of fibroblasts and/or vascular smooth muscle cells are well established. Markers that can be monitored and selected for in vascular smooth muscle cells are smooth muscle cell-specific $\alpha$ actin ($\alpha$SMC), calponin, smooth muscle myosin heavy chain (SM-MHC) or $\beta$-tubulin. Fibroblasts can be identified morphologically and selected for vimentin expression. Selection can be accomplished by fluorescence activated cell sorting (FACS), magnetic activated cell sorting (MACS), western blotting, or by other techniques known by those skilled in the art.

Step 330 shown in FIG. 2 allows for the option of modifying the fibroblasts and/or vascular smooth muscle cells, such as genetically altering or engineering the cells or expanding the cell population in vitro. Methods for genetic engineering or modifying cells are known to those with skill in the art (see, generally, Maniatis, Fritsch & Sambrook, *Molecular Cloning: A Laboratory Manual* (1982); and *DNA Cloning: A Practical Approach, Volumes I and II* (D. N. Glover, ed. 1985)). To genetically engineer the fibroblasts and/or vascular smooth muscle cells, the fibroblasts and/or vascular smooth muscle cells may be stably or transiently transfected or transduced with a nucleic acid of interest using a plasmid, viral or alternative vector strategy. Nucleic acids of interest include, but are not limited to, those encoding gene products that produce or enhance the production of extracellular matrix components found in fibroblasts and/or vascular smooth muscle tissue such as cytokines or growth factors, factors that enhance vascular health and elasticity such as proteolytic inhibitors, or biological response modulators such as ascorbic acid (vitamin C) or retinoic acid (vitamin A) that alter the secretory properties of fibroblasts and vascular smooth muscle cells to increase collagen type I and III and elastin production. For example, since tissue repair naturally occurs in an extracellular matrix environment rich in glycosamines and glycoproteins, it may make sense to genetically engineer the fibroblasts and/or vascular smooth muscle cells to produce one or more such compounds.

Alternatively or in addition, it has been shown that medial thinning and breakdown of elastin and collagen in the aorta is due, at least in part, to the effects of matrix metalloproteinases (MMPs). MMPs (MMP2, gelatinase A; MMP9, gelatinase B, and MMP 12, metalloelastase) are a group of proteolytic enzymes associated with the extracellular matrix. MMPs are known to degrade one or more connective tissue elements and have been implicated in clearing a path through the extracellular matrix for cell migration. Thus, in one aspect, the fibroblasts or smooth muscle cells may be engineered to inhibit the progression of an established (pre-existing) aneurysm by, e.g., inhibiting MMPs. Suitable inhibitors may include, for example, endogenous inhibitors, such as tissue inhibitors of MMPs (TIMPs) and macroglobulins, and synthetic inhibitors, such as chelating agents (e.g., EDTA and 1,10-phenanthroline), peptides, antibodies, and antibiotics such as tetracycline and its derivatives.

The maximal dosage of a bioactive agent such as an MMP inhibitor in this context is the highest dosage of the bioactive agent that effectively inhibits elastolytic anti-aneurysmal activity, but does not cause undesirable or intolerable side effects. The practitioner is guided by skill and knowledge in the field, and the present invention includes without limitation dosages that are effective to achieve the described phenomena.

The transduction of viral vectors carrying genes for bioactive compounds into the stem cells can be performed with viral vectors (adenovirus, retrovirus, adeno-associated virus, or other viral vectors) that have been isolated and purified. In such techniques, stem cells are exposed to the virus in serum-free media in the absence or presence of a cationic detergent for a period of time sufficient to accomplish the transduction.

Alternatively, vectors carrying genes for bioactive compounds can be introduced into the stem cells by use of calcium phosphate DNA precipitation, cationic detergent methods, liposomes, TAT-derived cell penetrating peptides, or in three-dimensional cultures by incorporation of the plasmid DNA vectors directly into a biocompatible polymer. Perioperative stem cell transfection may include ultrasound, magnetic field mediated-, or electorporation techniques. Electroporation protocols are known in the art and also can be found, e.g., in Maniatis, Fritsch & Sambrook, *Molecular Cloning: A Laboratory Manual* (1982); and *DNA Cloning: A Practical Approach, Volumes I and II* (D. N. Glover, ed. 1985. For the tracking and detection of functional proteins encoded by the introduced genes, the viral or plasmid DNA vectors can contain a readily detectable marker gene, such as green fluorescent protein or the beta-galactosidase enzyme, both of which can be tracked by histochemical means.

Another method for modifying the stem cells, smooth muscle cells, and/or fibroblasts prior to delivery to the aneurysmal sac is to expand the vascular smooth muscle stem cell population. Basically, the expansion process is accomplished by prolonged in vitro culturing of the stem cells in the selective cell culture medium (i.e., the medium that stimulated fibroblast or vascular smooth muscle stem cell growth without differentiation) from several to many successive cell passages. On the other hand, because adipose tissue yields a relatively large number of stem cells, if adipose tissue is used, in vitro expansion typically is not necessary.

Step 340 of FIG. 2 is another optional step that provides combining the stem cells to be delivered to the blood vessel with a carrier or scaffold. Many strategies in tissue engineering have focused on the use of biodegradable polymers as temporary scaffolds for cell transplantation or tissue induction. The success of a scaffold-based strategy is highly dependent on the properties of the material, requiring at a minimum that it be biocompatible, easy to sterilize, and, preferably, degradable over an appropriate time scale into products that can be metabolized or excreted. Mechanical properties are also important in polymer scaffold design for the regeneration tissues such as connective tissue, adipose tissue or blood vessels. In addition, scaffold degradation rates should be optimized to match the rate of tissue regeneration. Ideally degradable scaffolding polymers should yield soluble, resorbable products that do not induce an adverse inflammatory response. Alternatively, biodegradable scaffolds fabricated from naturally occurring elements, such as collagen, fibrin, hyaluronic acid, with or without growth factors connected to the backbone can be used as cell carriers. For general information regarding tissue engineering, see Ochoa and Vacanti, *Ann. N.Y. Acad. Sci.*, 979:10-26 (2002); Chaikof, et al., *Ann. N.Y. Acad. Sci.*, 961:96-105 (2002); Griffith, *Ann. N.Y. Acad. Sci.*, 961:83-95 (2002); Weiss, et al., U.S. Pat. No. 6,143,293; and Zdrahala, et al., U.S. Pat. No. 6,376,742.

In addition to porous scaffolds, the present invention contemplates using a gel scaffold. Such gels may be synthetic or semisynthetic gels that may not only stimulate cells through inclusion of adhesion and/or growth factor moieties, but may also respond to cells by degrading in the presence of specific cell cues. In one particularly well-developed family of gels known in the art, the basic macromer unit is a linear or branched polyethylene oxide end-capped with chemically reactive groups. Such a gel is particularly flexible for use in embodiments according to the present invention as it is intrinsically non-adhesive for cells and the gel properties can be tailored: the consistency of the gel can be controlled by the size of the monomers and the gel thickness; controlled degradation may be had by including hydrolysable polyester segments or enzyme-cleavable peptides at the chain ends, and adhesion peptides can be included in the gel at a concentration to control cell interactions.

Another type of gel useful in the present invention is a stimuli-responsive polymer gel. Stimuli-responsive polymer gels are compounds that can be triggered to undergo a phase-transition, such as a sol-gel transition. This property aids in reducing the pressure required to get the polymer-cell suspension through the delivery means. A preferred system would be a polymer-scaffolding system that is liquid at room temperature and gels at a temperature slightly below body temperature.

As described previously, stem cells respond to soluble bioactive molecules such as cytokines, growth factors, and angiogenic factors and can be engineered to secrete such factors as well as metalloproteinase inhibitors. Thus, these molecules alone can be used for tissue induction or growth. Alternatively, the tissue-inductive factors or MMP inhibitors can be incorporated into the biodegradable polymer of the scaffold, as an alternative to or in addition to engineering the stem cells to produce such inductive factors. In yet another alternative, biodegradable microparticles or nanoparticles loaded with these molecules can be embedded into the scaffold substrate.

Alternatively, embodiments of the present invention provide implanting stem cells along with the differentiation factors appropriate to induce fibroblast or vascular smooth muscle stem cell differentiation; however, if such factors are used they are preferably administered in a time release fashion.

Thus, the cells can be delivered with or without a cellular scaffolding or matrix element. However, in addition, the cells and scaffolding, if present, likely will be delivered in a pharmaceutically acceptable solution or diluent. For example, the cells may be delivered in a carrier of sterile water, normal saline, culture medium or other pharmaceutically acceptable carrier, alone or in combination with a pharmaceutically acceptable auxiliary substance, such as a pH adjusting or buffering agent, tonicity adjusting agent, stabilizer, wetting agent, and the like.

Alternate embodiments of this invention include encapsulating the cells in biodegradable microspheres or capsules, designed for gradual or measured release over time.

Referring again to FIG. 2, once stem cells have been isolated and/or expanded, they can be delivered to the blood vessel. To do so, several alternative delivery means may be employed. For example, syringes or microneedles may be used to deliver the stem cells directly to the wall of the blood vessel. Alternatively, catheters or other apparatus that function to deliver fluids into the walls of blood vessels may be employed. For example, Jacobsen, et al., U.S. Pat. No. 6,302,870, describe an apparatus for injecting fluids into the walls of blood vessels comprising a plurality of laterally-placed flexible needles disposed within a catheter. Similarly, Linden, et al., U.S. Pat. No. 5,538,504, describe a drug delivery catheter that comprises an elongated tubular shaft with a vessel puncturing element that remains retracted while the catheter is being deployed, and is then advanced to a protruding position at the site where the vessel is to be treated. Also, Makower, et al., U.S. Pat. No. 6,190,353, disclose a similar device for performing drug or other delivery procedures at specific locations in a blood vessel using a catheter comprising a deployable element that can penetrate the wall of the vessel. As another alternative, the cells may be delivered through a wrap comprised of cells embedded within a matrix or scaffold, applied either periadventially or intralumenally. Alternatively, in order to promote the survival of transplanted cells, chronic cell delivery may be needed. In such an embodiment, programmable, refillable pumps may be employed to deliver cells, or cell compositions, that include bioactive agents to the affected region. As shown by Hartlaub, U.S. Pat. No. 6,348,050, pump-based infusion systems may be used to gradually monitor cells, together with the appropriate biological response modulators, to create and maintain the optimal microenvironment for ensuring cell survival and function.

Figure 3:
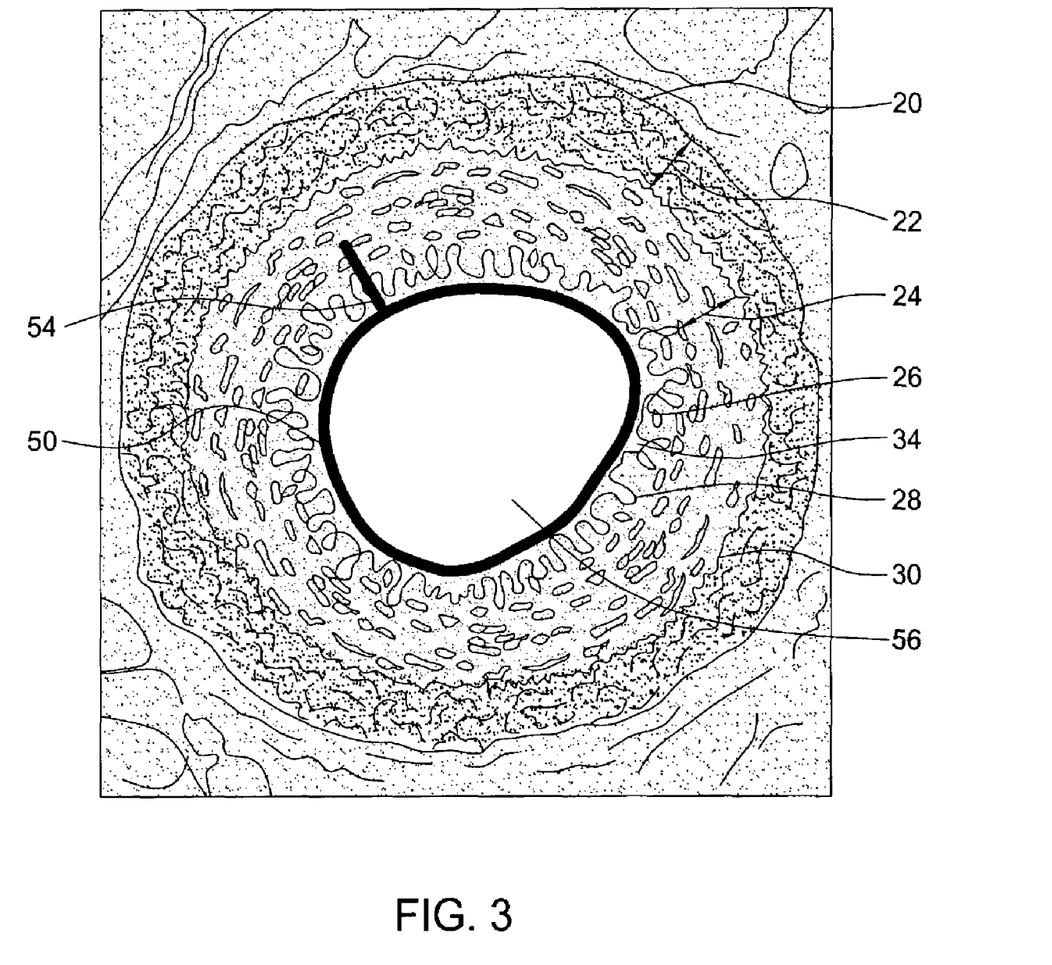
FIG. 3 is a partial sectional view of a blood vessel with vascular smooth muscle cells delivered thereto.

FIG. 3 shows a horizontal cross section of an artery. FIG. 3 shows an artery (20), having a tunica intima (26) adjacent to an internal or inner elastic lamina (28). The tunica media (24) in FIG. 3 is reduced in size, as compared to a normal artery, due to degeneration of the smooth muscle and elastic fibers of the tunica media layer. Encircling the tunica media (24) is the outer or external elastic lamina (30), the tunica adventitia (22), and the outer elastic lamina (30). In addition to the cross section of the catheter (50), an area between the catheter (50) in the lumen (34) of the artery and the intima layer (26) is present, as well as the inner lumen of the catheter (56). Also, there is a delivery means (54) seen in cross section projecting from the catheter (50).

In some procedures where vessel repair is necessarily extensive—particularly at aneurismal sites—a stent graft may be used, and a catheter may be tracked along side the stent to deliver the stem cells to the media of the vessel. Such stents are known in the art. In some cases, it may be preferable to use a biodegradable stent. Such devices are disclosed, for example in Jadhav, U.S. Pat. No. 6,368,346; and Healy, et al., U.S. Pat. No. 5,670,161. in such cases, where the discease is an an advanced stage and a stent graft is employed, cells with or without scaffolds, gels or encapsulation may be injected directly into the aneurysmal sac region for the purpose of remodeling and/or reinforcement.

Figure 4:
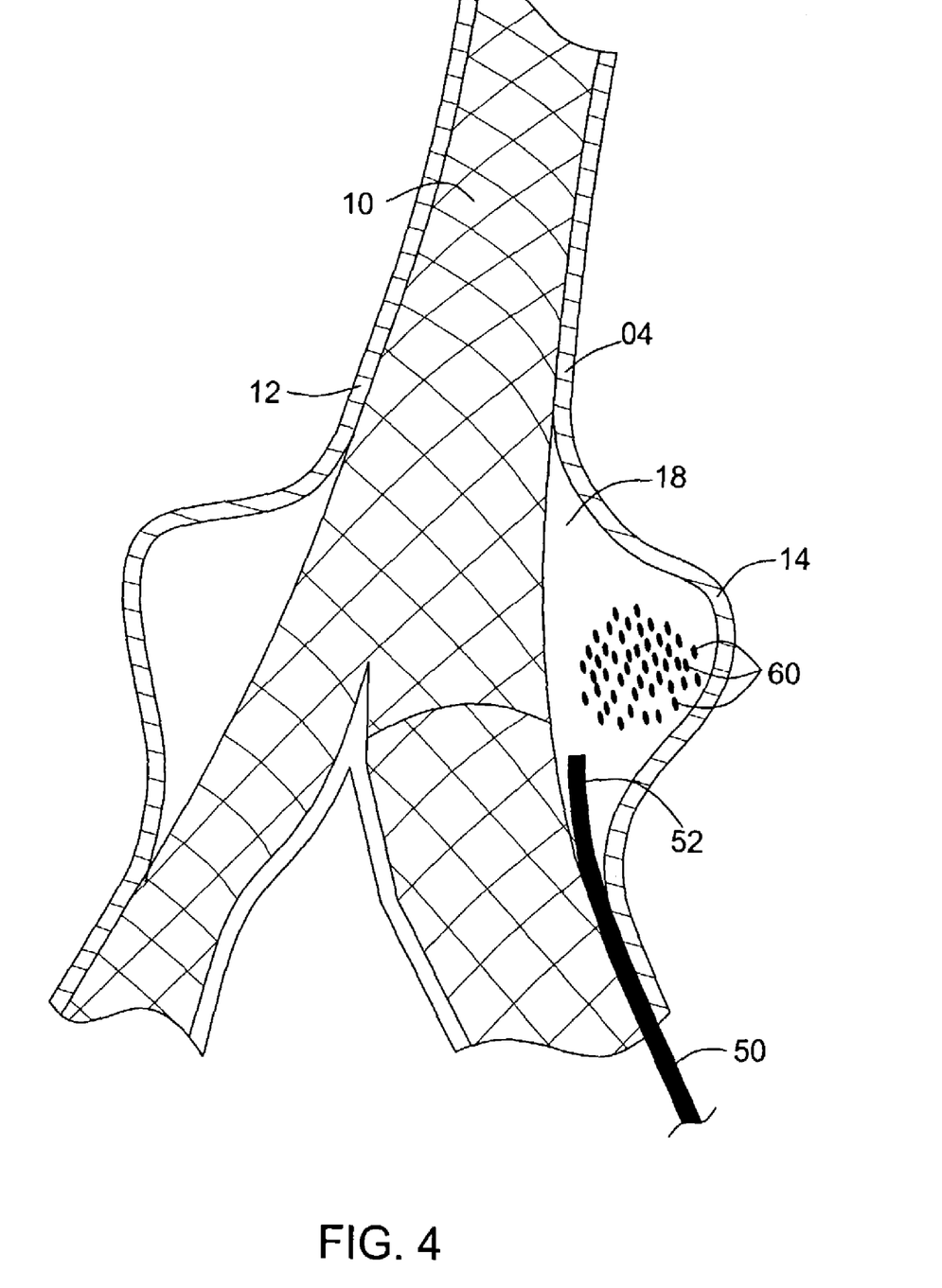
FIG. 4 is a partial sectional view of a descending aorta with a bifurcated stent graft placed therein, and a delivery catheter and stem cells delivered to an aneurismal sac.

FIG. 4 shows one embodiment of delivery of the stem cells, smooth muscle cells, or fibroblasts involving the transluminal placement of a prosthetic arterial stent graft 10 positioned in an aorta 12. The stent spans, within the aorta 12, an aneurysmal portion 14 of the aorta 12. The aneurysmal portion 14 is formed due to a bulging of the aorta wall 04. As a result, an aneurysmal sac 18 is formed of distended vessel wall tissue. The stent graft 10 is positioned spanning the sac 18 providing both a passageway for blood flow through the aorta 12 and sealing of the aneurysmal portion 14 of the aorta 12 from additional blood flow from the aorta 12. In addition, FIG. 4 shows a portion of a catheter 30 tracked along side of the stent graft 10. The catheter 30 has a distal end 32 that resides in the aneurysmal portion 14 of the aorta 12. The cells 60 are delivered to the aneurysmal site through the distal end 52 of the catheter 50. As discussed, the cells delivered may or may not be bioengineered, and may or may not be accompanied by cellular scaffolding, delivery solutions and/or soluble bioactive molecules such as cytokines, growth factors, and angiogenic factors. The cells and other elements, if present, support or bolster the aneurysm, while providing the factors necessary to stimulate the growth of new tissue to continue to support the aneurysm.

EXAMPLES

Cultivation of Smooth Muscle Progenitor Cells

Smooth muscle progenitor cells may be isolated from human blood, as demonstrated by Simper, et al. (see, *Circulation*, 106:1199-1204 (2002)). To do so, human mononuclear cells are isolated from peripheral buffy coat blood, suspended in endothelial growth medium (EGM-2) and seeded on collagen type I matrix. The seeded smooth muscle progenitor cells were then grown in platelet-derived growth factor BB-enriched medium to promote smooth muscle outgrowth and expansion. Evaluations of cell phenotype may be carried out by western blotting or FACS sorting using monoclonal antibodies to αSMA, human smooth muscle myosin heavy chain, calponin and Flt1, CD 31, VE cadherin, vWF, CD34, Tie-2 and Flk1 receptors. Smooth muscle outgrowth cells are positive for smooth muscle cell-specific α actin (αSMA), myosin heavy chain, calponin, and CD34, Flt1 and Flk1 receptors. CD31, VE cadherin, vWF, and Tie-2 serve to identify contaminating (non-vascular smooth muscle) cell types.

Cultivation of Fibroblasts

Fibroblasts may be isolated from human dermal tissue, as demonstrated by Tonello, et al. (see, *Biomaterials* 24:1205-1211(2003)). In this protocol, following epithelial sheet dispase removal, the dermis is cut into small pieces (2-3 mm2) and fibroblasts are isolated by sequential trypsin and collagenase digestion. The cells are then cultured with DMEM medium supplemented with 10% fetal bovine serum plus L-glutamine (2 mM) and penicillin(100 U/ml)/streptomycin (100 μg/ml). The medium is changed every three days and the cells are harvested by trypsin treatment.

Differentiation Protocol

For the development of stem cells into differentiated vascular smooth muscle cells, the stem cells may be cultivated in 3-dimensional aggregates called embryoid bodies (EBs) by the hanging drop method, by mass culture, or by differentiation in methylcellulose. Here, the hanging drop method is described.

1. Prepare a cell suspension containing a defined ES cell number of 800 cells in 20 mL of differentiation medium (DMEM (Gibco cat. No. 42200-030) supplemented with 20% FCS and, for each 100 mL medium, 1 mL 200 mM L-glutamine, 1 mL β-mercaptoethanol, 1 mL of nonessential amino acids stock (100×, Gibco cat. No. 25030-024)).

2. Place 20 mL drops (n=50-60) of the ES cell suspension on the lids of 100-mm bacteriological Petri dishes containing 10 mL PBS.

3. Cultivate the ES cells in hanging drops for 2 days. The cells will aggregate and form one EB per drop.

4. Rinse the aggregates carefully from the lids with 2 mL of medium, transfer into a 60-mm bacteriological Petri dish with 5 mL of differentiation medium, and continue cultivation in suspension for 7 days until the time of plating.

5. Plate EBs at day 7 and induce differentiation of vascular smooth muscle cells by treatment with $10^{-8}$ M retinoic acid (in ethanol or DMSO) and $0.5 \times 10^{-3}$ M db-cAMP between day 7 and 11 after plating (duration and treatment time has to be optimized for each cell line). The first spontaneously contracting vascular smooth muscle cells, which express the vascular-specific splice variant of the vascular smooth muscle myosin heavy chain (MHC) gene, appear in the EBs around 1 week after plating. Change the medium during the differentiation period every day or every second day.

6. A similar vascular smooth muscle cell induction is achieved by cultivating stem cells (n=600) as EBs in hanging drops in differentiation medium II (DMEM supplemented with 15% dextran-coated charcoal-treated FCS, and, for each 100 mL medium, 1 mL 200 mM L-glutamine, 1 mL β-mercaptoethanol, 1 mL of nonessential amino acids stock (100×, Gibco cat. No. 25030-024), 10 μL of a 3×10–4 M stock solution of Na-selenite, 2.5 mL of 7.5% stock solution bovine serum albumin, and 0.25 mL stock solution (4 mg/mL) transferrin) containing 2 mg/mL transforming growth factor β1 from day 0 to 5. Plate the EBs at day 5. The first spontaneously contracting vascular smooth muscle cells appear in EBs 10 days after plating, and maximal vascular smooth muscle cell differentiation (60%) is achieved at day 5 plus 24 hours to day 5 plus 28 hours.

7. Alternatively, ES cells (n=400) may be differentiated in hanging drops in M15 (DMEM plus 15% FCS, 0.1 mM beta-mercaptoethanol, 2 mM L-glutamine, 0.05 mg/mL streptomycin, and 0.03 mg/mL penicillin). After plating at day 4.5, the medium is partially exchanged every third day. Maximal vascular smooth muscle cell differentiation (30%) is achieved at day 4.5 plus 17 hours to day 4.5+19 hours.

8. For morphological analysis, transfer a single EB into each well of gelatin (0.1%)-coated microwell plates, transfer 20 to 40 EBs per dish onto 60-mm tissue culture dishes containing 4 coverslips (10×10 mm) for immunofluorescence, or transfer 15 to 20 EBs onto 60-mm tissue culture dishes for reverse transcription PCR (RT-PCR) analysis of EB outgrowths.

While the present invention has been described with reference to specific embodiments, it should be understood by those skilled in the art that various changes may be made and equivalents may be substituted without departing from the true spirit and scope of the invention. In addition, many modifications may be made to adapt a particular situation, material, or process to the objective, spirit and scope of the present invention. All such modifications are intended to be within the scope of the invention.

All references cited herein are to aid in the understanding of the invention, and are incorporated in their entireties for all purposes.

The invention claimed is:

1. A method of treating an aneurysm in an individual at the aneurysmal site using self-derived cells, comprising:

harvesting smooth muscle cell-containing tissue from the individual wherein said tissue is selected from the group consisting of adipose tissue, bone marrow and peripheral blood;

isolating smooth muscle cells from the tissue;

delivering the isolated smooth muscle cells directly to the wall of a blood vessel at said aneurysmal site by liquid delivery means wherein said blood vessel wall is repaired and said aneurysm is treated in said individual.

2. The method of claim 1, wherein the harvesting step is accomplished by liposuction, drawing blood, or harvesting bone marrow.

3. The method of claim 1, wherein the smooth muscle cells are isolated by growth in selective medium, by density centrifugation, fluorescence activated cell sorting or by magnetic activated cell sorting.

4. The method of claim 1, wherein the smooth muscle cells are isolated by assaying for smooth muscle cell-specific α actin, calponin, smooth muscle myosin heavy chain, β-tubulin or vimentin expression.

5. The method of claim 1, further comprising the step of modifying the smooth muscle cells after the isolating step.

6. The method of claim 5, wherein the modifying step is accomplished by genetic engineering.

7. The method of claim 6, wherein the smooth muscle cells are genetically engineered to produce at least one cellular factor selected from the group of collagen I, collagen III, elastin, cytokines, growth factors, metalloproteinase inhibitors, inhibitors of inflammation, vitamin A, vitamin C or angiogenic factors.

8. The method of claim 5, wherein the modifying step is in vitro culture expansion of the smooth muscle cells.

9. The method of claim 1, further comprising the step of combining the smooth muscle cells with scaffolding material after the isolating step.

10. The method of claim 9, wherein the scaffolding material is biodegradable.

11. The method of claim 9, wherein the scaffolding material promotes healing.

12. The method of claim 9, wherein the scaffolding material is a gel.

13. The method of claim 12, wherein the gel is a stimuli-responsive gel.

14. The method of claim 13, wherein the stimuli-responsive gel is biodegradable.

15. The method of claim 1, wherein the delivery means is a catheter, cannula, or microneedle.

16. The method of claim 1, wherein the smooth muscle cells to be delivered further comprise a carrier compound.

17. The method of claim 16, wherein the carrier compound is sterile water, normal saline, or culture medium, with or without bioactive agents.

18. A method of repairing an aneurysm in an individual using self-derived cells, comprising:

harvesting smooth muscle cell-containing tissue from the individual wherein said tissue is selected from the group consisting of adipose tissue, bone marrow and peripheral blood;

isolating smooth muscle cells from the tissue;

delivering the isolated smooth muscle cells directly to the wall of a blood vessel at the aneurysm site by a fluid delivery means wherein the blood vessel wall at said aneurysm site is repaired and said aneurysm is treated in said individual.

19. The method of claim 18, wherein the smooth muscle cells are genetically engineered to produce at least one cellular factor selected from the group of collagen I, collagen III, elastin, cytokines, growth factors, metalloproteinase inhibitors, inflammation inhibitor, vitamin A, vitamin C or angiogenic factors.

* * * * *